United States Patent [19]

Arretz

[11] Patent Number: 4,943,662

[45] Date of Patent: Jul. 24, 1990

[54] PROCESS FOR PREPARATION OF DITHIOLS

[75] Inventor: Emmanuel Arretz, Pau, France

[73] Assignee: Societe Nationale Elf Aquitaine (Production), Courbevoie, France

[21] Appl. No.: 288,438

[22] Filed: Dec. 22, 1988

[30] Foreign Application Priority Data

Feb. 17, 1988 [FR] France .................................. 88 01881

[51] Int. Cl.$^5$ ............................................. C07C 148/00
[52] U.S. Cl. ........................................ 568/66; 568/57; 568/70
[58] Field of Search ............................ 568/57, 66, 70; 204/157.76

[56] References Cited

U.S. PATENT DOCUMENTS

| | | | |
|---|---|---|---|
| 3,069,472 | 12/1962 | Loev et al. ............................. | 568/69 |
| 3,591,475 | 7/1971 | Griesbaum et al. ............ | 204/157.76 |
| 3,686,326 | 8/1972 | Oswald et al. ................... | 204/157.76 |
| 4,140,604 | 2/1979 | Dimmig ........................... | 204/157.76 |
| 4,233,128 | 11/1980 | Allivier et al. ................. | 204/157.76 |
| 4,313,006 | 1/1982 | Hager ..................................... | 568/70 |
| 4,396,778 | 8/1983 | Hager ..................................... | 568/70 |

FOREIGN PATENT DOCUMENTS

| 47021 | 3/1982 | European Pat. Off. . |
|---|---|---|
| 82500 | 6/1983 | European Pat. Off. . |

*Primary Examiner*—Mary E. Ceperley
*Attorney, Agent, or Firm*—Stevens, Davis, Miller & Mosher

[57] ABSTRACT

The invention relates to the synthesis of dithiols and more particularly that of $\alpha,\omega$-dithiols having 5 to 20 carbon atoms.

The process according to the invention comprises reacting a di-(tertiary-alkylthio)alkane with hydrogen sulphide in the presence of a solid acid catalyst. The alkane dithiol is obtained selectively and a tertiary-alkyl mercaptan is obtained as by-product. It is possible to reuse the latter in a cyclical process to produce the original di-(tertiary-alkylthio)alkane.

20 Claims, No Drawings

PROCESS FOR PREPARATION OF DITHIOLS

FIELD OF THE INVENTION

The present invention relates to the synthesis of dithiols and the preparation of α,ω-dithiols having 5 to 20 carbon atoms.

BACKGROUND OF THE INVENTION

Obtaining dithiols by the reaction of an alkyl dihalide with an alkaline salt of $H_2S$, directly or via a bis-thiocyanate, bis-thiourethane or bis-thioacetate comprises several stages. The yields from reactions leave something to be desired. See N. KARASH, *Organic Sulfur Compounds*, vol. 1, pp. 199–207 (1961).

The photochemical process which comprises reacting $H_2S$ with an olefin in the presence of a catalytic system comprising a benzophenone or thiobenzophenone and a trialkyl phosphite gives excellent results with monoolefins. See French Pat. No. 2,424,907 and European Pat. No. 60,754. Unfortunately, for dienes, secondary reactions occur which spoil the yield of the desired dithiol (formation of polymers by interaction of the dithiol with the diene). To limit these secondary reactions, particular operating conditions have been recently disclosed in French Patent Application No. 86/17,640. The aim is to have a very large excess of hydrogen sulphide in the reaction medium.

Another access route to dithiols, particularly to 1,4-butanedithiol from butadiene, is described in U.S. Pat. No. 3,069,472. The reaction scheme disclosed in this patent comprises a free radical or photochemical addition of a tertiary-alkyl mercaptan to butadiene to form a 1,4-di-(tertiary-alkylthio)butane which, by splitting in the presence of a suitable catalyst, gives 1,4-butanedithiol. This splitting reaction provides, as a by-product, the olefin corresponding to the structure of the original tertiary mercaptan. This olefin is not directly reusable in a cyclical process and is moreover susceptible to oligomerization upon splitting.

A process has now been found whose principal advantages are a much higher yield and selectivity of dithiols, the absence of by-products of the dithiol such as polysulphides, and the simultaneous regeneration of one of the compounds leading to the original product.

The preceding references are hereby incorporated by reference.

DETAILED DESCRIPTION OF THE INVENTION

The process for the preparation of dithiols according to the invention is characterized in that hydrogen sulphide is reacted, in the presence of a solid acid catalyst, with a di-(tertiary-alkylthio)alkane of general formula:

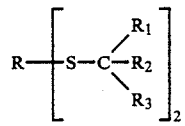

(I)

in which R is an alkylene radical having 5 to 20 carbon atoms, and the symbols $R_1$, $R_2$ and $R_3$ are identical or different and are each an alkyl radical having 1 to 15 carbon atoms.

The sulphydrolysis reaction according to the invention may be schematically shown as follows:

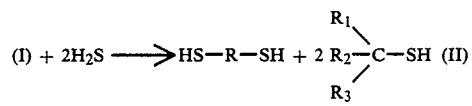

It produces the desired dithiol HS—R—SH and a tertiary mercaptan $R_1R_2R_3C$—SH which can be reused in a cyclical manner for synthesizing the original di-(tertiary-alkylthio)alkane (I).

The sulphydrolysis may be carried out at a temperature within the range of ambient temperature to 250° C., but preferably at a temperature in the range of 85° C. to 200° C. To significantly improve the yield and avoid secondary reactions, the reaction is advantageously carried out under pressure, the organic reactant being in the liquid state. Pressures of 5 to 30 bars, and particularly 10 to 20 bars, are particularly favorable. It is advantageous to operate using excess hydrogen sulphide in relation to the stoichiometric quantity. Thus, it is recommended to operate using 2 to 12 moles of $H_2S$ (preferably 4 to 8 moles) per mole of di-(tertiaryalkylthio)alkane used.

Among solid acid catalysts, natural aluminosilicates and synthetic aluminosilicates, such as the zeolites, or else ion exchange resins which are strongly acidic are preferred. Examples of natural aluminosilicates which may be mentioned are the silica-aluminas having a content of alumina of 1 to 20%, such as those produced by the Davison Chemical Company, and the acid derivatives of the montmorillonite of the general structure:

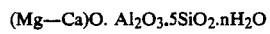

marketed under the trademark FILTROL.

As far as zeolites are concerned, those of types X and Y are preferred. The sodium content of which, expressed as $Na_2O$, is less than 15% by weight and advantageously less than 3%.

As ion exchange resins, the acid cationic exchange resins are preferred which have a polymeric aromatic structure (polystyrene and divinylbenzene) or a perfluorinated aliphatic structure, containing sulphonic groups. These resins, which may be used in bulk or bound to an inorganic or organic substrate, have the commercial tradenames AMBERLITE, AMBERLYST, LEVATIT, DOWEX, DUOLITE and NAFION.

Phosphoric acid impregnating a substrate may equally serve as a catalyst for the sulphydrolysis according to the invention.

The tertiary mercaptan (II) is preferably selected from those whose boiling point is sufficiently different from that of the final dithiol so that their separation by distillation is simple and facilitates the recycling of the tertiary mercaptan for the synthesis of the di-(tertiaryalkylthio)alkane. The following tertiary mercaptans are exemplary: tertiary-butyl mercaptan (B.P. 66° C.), tertiary-octyl mercaptan (B.P. 150° C.), tertiary-nonyl mercaptan (B.P. 189°–210° C.), tertiary-dodecyl mercaptan (B.P. 228°–246° C.), and tertiary-hexadecyl mercaptan (B.P. 277°–316° C.).

The di-(tertiary-alkylthio)alkanes (I) of the process according to the invention may be advantageously prepared by the photochemical addition of two molecules of a tertiary mercaptan of formula (II) to one molecule of a nonconjugated diene having at least 5 carbon atoms.

This photochemical addition of the Karash type may be carried out at atmospheric pressure by irradiation, using a lamp which emits in the ultraviolet (200 to 400 nm), of a liquid mixture of the nonconjugated diene and an excess of the tertiary mercaptan (II), preferably in proportions such that the molar ratio of tertiary mercaptan to diene is in the range of 2 to 4.

The photochemical reaction may be carried out at moderate temperatures, generally within the range −10° C. to +60° C. (preferably in the range of 20° C. to 50° C.), and may be carried out in the absence of a catalyst. However, to improve the yield and the productivity of the reaction, it is preferable to operate in the presence of a specific catalyst comprising either an aromatic ketone in association with an organic phosphite or an organic phosphine, or comprising certain derivatives of acetophenone, or else comprising a benzoyl phosphine oxide.

As aromatic ketones which can be used, there may be mentioned benzophenone and derivatives of benzophenone comprising, on one or both benzene rings, substituents such as halogen atoms or alkyl, alkoxy or alkylthio groups, as well as xanthenic compounds of the formula:

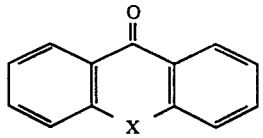

(III)

in which X is an oxygen atom or a sulphur atom and the benzene rings may carry up to three halogen, alkyl or aryl substituents. These ketones are used mixed with an organic phosphite, preferably a trialkyl phosphite such as trimethyl phosphite, tributyl phosphite, tridodecyl phosphite, or with an organic phosphine such as trimethyl phosphine, triethyl phosphine or tributyl phosphine.

As acetophenone derivatives which can be used as a catalyst, there may be mentioned more particularly α,α-di-alkoxy-α-phenylacetophenones, α-alkoxy-α-phenylacetophenones, α,α-dialkoxyacetophenones, α,α-dialkyl-α-hydroxyacetophenones and α,α-dialkyl-α-morpholinoacetophenones, the alkoxy and alkyl groups of which may contain 1 to 8 carbon atoms, as well as their substituted derivatives on the benzene ring or rings, for example by alkyl, alkoxy or alkylthio groups.

As catalysts of the benzoyl phosphine oxide type, there may be mentioned those of the formula:

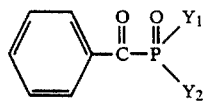

(IV)

in which the benzene ring may carry various substituents such as, for example, alkyl, alkoxy or alkylthio groups, and the symbols $Y_1$ and $Y_2$ are aliphatic or aromatic hydrocarbon groups.

Where the catalytic system is a mixture of an aromatic ketone and an organic phosphite or an organic phosphine, the concentrations to be used for each of these constituents are in the range 0.005 to 0.1 mole per liter of diene used. For the other catalysts (acetophenones, benzoyl phosphine oxides), the concentrations to be used are in the range 0.0001 to 0.1 mole per liter of diene.

The process according to the invention may be generally used for the preparation of dithiols from nonconjugated dienes having 5 to 20 carbon atoms. In particular, very useful dithiols, carrying an SH group at each extremity of their hydrocarbon chain, are obtained from α,ω-dienes. As nonlimiting examples of α,ω-dienes of this type, there may be mentioned pentadiene, hexadiene, octadiene, decadiene, undecadiene, dodecadiene, hexadecadiene and eicosadiene.

Each of the two stages (photochemical addition and sulphydrolysis) may be carried out discontinuously or continuously. However, in the most practical mode of operation, the process is carried out continuously and may function as a cyclical process in which the tertiary mercaptan (II), formed at the sulphydrolysis stage at the same time as the desired dithiol, is recycled to the photochemical reaction vessel which is being used for producing di-(tertiaryalkylthio)alkane by reaction with the nonconjugated diene.

EXAMPLES

The following examples illustrate the invention without limiting it.

EXAMPLE 1: 1,6-HEXANEDITHIOL (a) Preparation of 1,6-di-(tertiary-butylthio)-hexane The addition of tertiary-butyl mercaptan to 1,5-hexadiene according to the reaction:

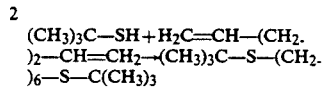

is carried out in a reaction vessel comprising a stainless steel cylinder, having a usable volume of 300 ml. In the axis of this cylinder is fixed a coaxial quartz tube containing a mercury vapor lamp. The maximum emission of which is at a wavelength of 350 nm.

Cooling and stirring of the liquid medium are ensured by an external loop, comprising a recirculating pump and a heat exchanger which allow the temperature of the medium to be maintained at 25°±2° C.

Into the reaction vessel there is introduced, per hour, a mixture of 270 g (3 moles) of tertiary-butyl mercaptan and 82 g (1 mole) of 1,5-hexadiene containing 128 mg of α,α-dimethoxy-α-phenylacetophenone (which is approximately 0.004 mole per liter of diene). The output of liquid leaving the reaction vessel is measured and analyzed by gas phase chromatography. The conversion ratio of 1,5-hexadiene is 96%. The production rate of 1,6-di-(tertiary-butylthio)hexane is 246 g per hour, corresponding to a yield of 94% based on the 1,5-hexadiene used. The excess of mercaptan and the nonconverted 5-hexadiene are removed by distillation and may be recycled to the head of the reaction vessel.

By repeating this operation, but using different catalysts, the results assembled in the following table are obtained:

| CATALYTIC SYSTEM (MOLE/LITER OF HEXADIENE) | CONVERSION OF HEXADIENE (%) | YIELD OF 1,6-DI-(TERTIARY-BUTYLTHIO)-HEXANE (%) |
|---|---|---|
| α,α-Dimethyl-α-phenylacetophenone (0.004) | 96 | 94 |
| α-Methoxy-α-phenylacetophenone (0.004) | 88 | 86.1 |
| α-Methoxy-α-phenylacetophenone (0.01) | 92 | 90 |
| α,α-Dimethyl-α-hydroxyacetophenone (0.004) | 86.7 | 84.9 |
| α,α-Diethoxyacetophenone (0.004) | 85 | 83 |
| Benzophenone (0.01) + tributyl phosphite (0.02) | 65 | 63.6 |
| Thioxanthone (0.01) + tributyl phosphite (0.02) | 62 | 60.7 |

(b) Production of 1,6-hexanedithiol

To carry out the sulphydrolysis of 1,6-di-(tertiarybutylthio)hexane to 1,6-hexanethiol, a tubular reaction vessel of diameter 25 mm is used, having a usable capacity of 200 ml filled with a cation exchange resin, known under the trade name AMBERLYST 15, previously dried.

Through these contents are passed 52.4 g (0.2 mole) of 1,6-di-(tertiary-butylthio)hexane and 40.8 g (1.2 mole) $H_2S$ per hour.

The pressure inside the reaction vessel is maintained at 15 bars. The reaction is studied at different temperatures controlled by the circulation of oil, maintained at constant temperature, through a double envelope which surrounds the reaction vessel.

For each trial carried out at a defined temperature, the crude reaction product is analyzed. The conversion rate of the original 1,6-di-tertiary-butylthio)-hexane is thus established. The production rate and selectivity of 1,6-hexanedithiol, as well as the selectivity of the intermediate product produced in the sulphydrolysis are established. It corresponds to the conversion of one of the the two sulphide groups of 1,6-di-(tertiary-butylthio)-hexane (compound A) into 6-tertiary-butylthio-hexanethiol (compound B) which is converted, by recycling and possibly increasing the reaction temperature into the final dithiol.

These different reactions may be indicated schematically in the following way:

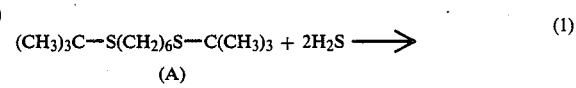

$$(CH_3)_3C-S(CH_2)_6S-C(CH_3)_3 + 2H_2S \longrightarrow \quad (1)$$
(A)

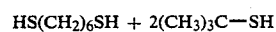

$$HS(CH_2)_6SH + 2(CH_3)_3C-SH$$

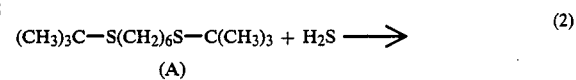

$$(CH_3)_3C-S(CH_2)_6S-C(CH_3)_3 + H_2S \longrightarrow \quad (2)$$
(A)

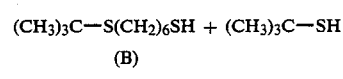

$$(CH_3)_3C-S(CH_2)_6SH + (CH_3)_3C-SH$$
(B)

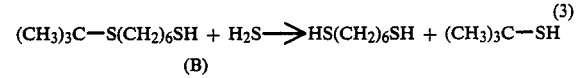

$$(CH_3)_3C-S(CH_2)_6SH + H_2S \longrightarrow HS(CH_2)_6SH + (CH_3)_3C-SH \quad (3)$$
(B)

The results are given in the following table:

| TEMPERATURE (°C.) | CONVERSION OF COMPOUND A | PRODUCTION OF HEXANEDITHIOL (g/h) | SELECTIVITY | |
|---|---|---|---|---|
| | | | HEXANEDITHIOL | COMPOUND B |
| 110 | 80.2 | 7.3 | 30.5 | 67.1 |
| 130 | 89 | 16 | 60 | 38 |
| 150 | 95 | 21.3 | 75 | 23 |

EXAMPLE 2

Example 1-b is repeated using the following reaction conditions:

| Catalyst charge: | 200 ml |
|---|---|
| Operating pressure: | 15 bars |
| Temperature: | 150° C. |
| Hourly input of: | |
| compound A: | 62.9 g/h |
| $H_2S$: | 49 g/h | with three different catalysts, namely AMBERLYST 15, FILTROL 71 and ZEOLITE Y-62 (marketed by UNION CARBIDE)

The results obtained are presented in the following table:

| CATALYST | CONVERSION OF COMPOUND A | PRODUCTION OF HEXANEDITHIOL (g/h) | SELECTIVITY | |
|---|---|---|---|---|
| | | | HEXANEDITIHIOL | COMPOUND B |
| AMBERLYST 15 | 91 | 23.6 | 72 | 26 |
| FILTROL 71 | 88 | 22.1 | 70 | 28 |

| CATALYST | CONVERSION OF COMPOUND A | PRODUCTION OF HEXANEDITHIOL (g/h) | SELECTIVITY HEXANEDITIHIOL | COMPOUND B |
|---|---|---|---|---|
| ZEOLITE Y-62 | 86 | 21.3 | 69 | 29 |

EXAMPLE 3: 1,10-DECANEDITHIOL (a) Preparation of 1,10-di-(tertiary-butylthio)-decane The operation is carried out as in Example 1-a, but introducing continuously, per hour, a mixture of 270 g of tertiary-butyl mercaptan, 138 g of 1,9-decadiene and 179 mg of α,α-dimethoxy-α-phenylacetophenone (which is 0.0038 mole per liter of diene).

The liquid mixture recovered from the exit port of the reactor corresponds to a conversion ratio of 1,9-decadiene of 91% and a production rate of 1,10-di-(tertiary-butylthio)decane of 276.7 g per hour, corresponding to a yield of 87% based on the 1,9-decadiene used. The excess of mercaptan and the nonconverted 1,9-decadiene are removed by distillation.

(b) Production of 1,10-decanedithiol

The operation is carried out as in Example 1-b with the reaction vessel charged with 200 ml of AMBERLYST 15 resin, previously dried. Through these contents are passed 63.6 g of 1,10-di-(tertiary-butylthio)decane and 40.8 g of $H_2S$ per hour. The pressure in the reaction vessel is maintained at 15 bars and the temperature at 140° C.

In this manner, 23 g of 1,10-decanedithiol are obtained per hour, which is a yield of 56% based on the 1,10-di-(tertiary-butylthio)decane of which 91% is converted. The remaining conversion is essentially represented by the 10-tertiary-butylthio-decanethiol resulting from the sulphydrolysis of a single sulphide group. This mercaptan sulphide can be easily separated from 1,10-decanedithiol by distillation and recycled in a further operation to be converted into the dithiol.

Although the invention has been described in conjunction with specific embodiments, it is evident that many alternatives and variations will be apparent to those skilled in the art in light of the foregoing description. Accordingly, the invention is intended to embrace all of the alternatives and variations that fall within the spirit and scope of the appended claims.

I claim:

1. A process for the preparation of dithiols comprising reacting hydrogen sulphide in the presence of a solid acid catalyst with a di-(tertiary-alkylthio) alkane of general formula:

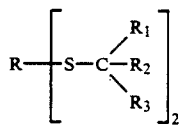

(I)

in which R is an alkylene radical having 5 to 20 carbon atoms, and the symbols $R_1$, $R_2$ and $R_3$ are identical or different and are each an alkyl radical having 1 to 15 carbon atoms and wherein the reaction temperature is within the range of ambient temperature to 250° C.

2. The process according to claim 1, wherein the solid acid catalyst has a sodium content, expressed as $Na_2O$, is less than 15% by weight.

3. The process according to claim 2, wherein the reaction temperature is in the range of 85° C. to 200° C.

4. The process according to claim 1, wherein reaction occurs at a pressure in the range of 5 to 30 bars.

5. The process according to claim 4, wherein the pressure is in the range of 10 to 20 bars.

6. The process according to claim 1, wherein 2 to 12 moles of $H_2S$ are used per mole of di-(tertiary-alkylthio) alkane.

7. The process according to claim 6, wherein 4 to 8 moles of $H_2S$ are used.

8. The process according to claim 1, wherein the solid acid catalyst is a natural aluminosilicate or a synthetic aluminosilicate or an ion exchange resin.

9. The process according to claim 1, wherein the di-(tertiary-alkylthio)alkane is a α,ω-di-(tertiaryalkylthio)alkane.

10. The process according to claim 1, wherein the tertiary mercaptan of formula:

(II)

produced as a by-product by the reaction is recycled for the preparation of the original di-(tertiary-alkylthio)alkane.

11. The process according to claim 10, wherein the tertiary mercaptan (II) is selected from those whose boiling point is sufficiently different from that of the final dithiol to allow their separation by simple distillation.

12. The process according to claim 10, wherein the tertiary mercaptan (II) is added photochemically to a nonconjugated diene having at least 5 carbon atoms.

13. The process according to claim 12, wherein 2 to 4 moles of tertiary mercaptan are used per mole of diene.

14. The process according to claim 12, wherein the photochemical addition is carried out at a temperature in the range of −10° C. to +60° C.

15. The process according to claim 14, wherein the temperature range is 20° C. to 50° C.

16. The process according to claim 12, wherein the photochemical addition is carried out in the presence of a catalyst chosen from derivatives of acetophenone, benzoyl phosphine oxides and combinations of an aromatic ketone with an organic phosphite or an organic phosphine.

17. The process according to claim 12, wherein the nonconjugated diene is a α,ω-diene having 5 to 20 carbon atoms.

18. The process according to claim 1, wherein the reaction is carried out continuously.

19. The process according to claim 2, wherein the sodium content is less than 3% by weight.

20. The process according to claim 1 wherein polysulphide by-products are absent.

* * * * *